United States Patent [19]

Kalt

[11] Patent Number: 5,755,232
[45] Date of Patent: May 26, 1998

[54] UNIVERSAL ANATOMICAL SUPPORT DEVICE AND METHOD OF USING SAME

[75] Inventor: Glenda Kalt, Boca Raton, Fla.

[73] Assignee: Medical Distributors, Inc., Boca Raton, Fla.

[21] Appl. No.: 752,266

[22] Filed: Nov. 19, 1996

Related U.S. Application Data

[60] Provisional application No. 60/014,286 Mar. 29, 1996.

[51] Int. Cl.⁶ ........................................ A61G 15/00
[52] U.S. Cl. ........................ 128/845; 128/858; 128/848
[58] Field of Search .................................. 128/845, 846, 128/857, 858, 848, 200.24, 204.45; 606/204.45, 191, 196, 199

[56] References Cited

U.S. PATENT DOCUMENTS

| | | |
|---|---|---|
| 310,565 | 9/1885 | Petruson . |
| 4,153,051 | 5/1979 | Shippert ........................ 128/89 R |
| 4,213,452 | 7/1980 | Shippert ........................ 128/89 R |
| 4,702,736 | 10/1987 | Kalt et al. . |
| 4,738,662 | 4/1988 | Kalt et al. . |
| 4,838,867 | 6/1989 | Kalt et al. . |
| 4,838,878 | 6/1989 | Kalt et al. . |
| 4,917,112 | 4/1990 | Kalt . |
| 4,919,654 | 4/1990 | Kalt . |
| 4,966,590 | 10/1990 | Kalt . |
| 5,000,741 | 3/1991 | Kalt . |
| 5,037,397 | 8/1991 | Kalt et al. . |
| 5,308,339 | 5/1994 | Kalt et al. . |
| 5,476,091 | 12/1995 | Johnson . |
| 5,479,944 | 1/1996 | Petruson . |
| 5,549,103 | 8/1996 | Johnson ........................... 128/848 |
| 5,553,605 | 9/1996 | Muchin ............................ 128/848 |

*Primary Examiner*—Michael A. Brown
*Attorney, Agent, or Firm*—Quarles & Brady

[57] ABSTRACT

An anatomical support device is disclosed that lifts, supports and stabilizes various parts of the human anatomy preferably utilizing a medical grade, hypoallergenic, removable tape base plate covered by a water resistant, sterilizable support fabric. The fabric is preferably a porous, non-woven material and/or loop material having sufficient tension and resiliency to gently support and stabilize nasal tissue to allow improved air flow without nasal irritation. When applied to other body parts, the device lifts and supports tissue to enhance appearance and well being.

16 Claims, 5 Drawing Sheets

UNIVERSAL ANATOMICAL SUPPORT DEVICE AND METHOD OF USING SAME

CROSS-REFERENCE TO RELATED APPLICATION

This application claims the benefit of United States provisional application Ser. No. 60/014,286, filed Mar. 29, 1996.

FIELD OF THE INVENTION

The present invention relates in general to an anatomical support device useful for supporting or lifting the tissue of various areas of a subject's anatomy. More particularly, the anatomical support is especially useful for lifting and stabilization of nose tissue to improve nasal air flow and to provide support to larger structures, such as breasts.

BACKGROUND OF THE INVENTION

It is often desirable and/or necessary to provide support, lift, or stabilization, to various areas of the human anatomy. It is important that the support device is adaptable to conform to the patient's body and tissue, and that it be easily removed with a minimum of discomfort to the patient.

Typically, adhesive tape has been used to provide lift and support to the tissue of various anatomical features. However, adhesive tape is generally not sufficiently rigid to support certain, particularly larger, parts, such as breasts, and has many disadvantages. For example, its holding capacity is greatly reduced within a few hours of application due to perspiration and body oils. Adhesive tape is not water resistant, and its holding power is diminished when saturated during showering, swimming or heavy perspiration.

Moreover, adhesive tape generally is not breathable, tending to damage or irritate the subject's skin. Adhesive tape can leave a residue that can clog pores and irritate skin. Also, removing adhesive tape can prove irritating to the patient's skin. Certain adhesive tapes are also not suitable for sterilization.

Other tissue support devices include elastic bandages. Elastic bandages generally do not allow adequate air flow to the wrapped skin surface, causing irritation and damage to the skin. Elastic bandages do not have securing mechanisms for preventing slippage from the supported area. Also, elastic bandages are not readily adapted for support of irregular shaped body parts such as noses and eyelids, without obstruction of breathing or sight. Further, elastic bands can be restrictive when wrapped around the area to be supported, and can be become more restrictive or too loose and unsupportive when wet.

It is desirable to provide universal anatomical support that can accommodate the lifting and stabilization of different body parts. One location on the human anatomy in need of tissue support is the nose. Many people have difficulty breathing through their nose due to congestion, allergies, asthma etc. A method of nostril support and stabilization can often help such difficult breathing problems. Further, difficulty in breathing can lead to nighttime snoring and a method of nostril support may alleviate this problem. Moreover, many athletes find that their breathing is enhanced when the nostrils are supported and nasal passages are expanded to allow improved air flow.

One approach to nasal dilation is shown in U.S. Pat. No. 5,476,901, issued to Johnson. The device comprises an adhesive strip having embedded truss members. The adhesive strip is placed over the nose and the truss members flex to dilate the nasal passages by pulling outwardly on the sides of the nose. However, this type of device may have a number of drawbacks due to the use of adhesives and the rigidity of the truss members. Also, the truss members in such a device may not easily conform to the many contours typically associated with anatomical features other than noses and may not accommodate different nose shapes without irritation.

Accordingly, there is a need for a universal anatomical support device which can be used to lift and/or support tissue on a wide variety of anatomical features in a variety of shapes. There is also a need for such a support device to have a hypoallergenic adhesive, be easy to remove from the skin, be able to conform to a variety of contours, be breathable to allow oxygen to reach the user's skin, and resist dislodgement when wet by water or perspiration. It is also desirable for such a support device to be sterilizable and suitable for use in an operating room.

SUMMARY OF THE INVENTION

One aspect of the present invention provides a method of lifting and stabilizing tissue of an anatomical feature on a subject comprising placing a support on the tissue of the anatomical feature wherein the support comprises a base means for adhering the support to the tissue, the base means having an inner surface carrying an adhesive for fixedly attaching the support to the tissue and an outer surface having fixedly attached thereto, on at least a portion thereof, an elastic substrate, wherein the elastic substrate includes a hook or loop material.

Preferably, the adhesive is hypoallergenic and the base means is porous. Advantageously, the anatomical feature is a nose. Preferably, the support is adhered and substantially centered over the nose between the bridge and end of the nose. The elastic substance preferably includes a porous, non-woven cover. The above method can also be used to advantageously support a breast, buttocks, finger, herniated area or other body area.

Alternatively, a top cover can comprise a flexible elastic hook or loop material that mates with the hook or loop material on the base to provide variable degrees of tension and associated tissue lift.

Another aspect of the present invention provides a support for lifting or supporting tissue of an anatomical feature on a subject comprising a base means for adhering the support to the tissue, the base means having an inner surface and an outer surface; an adhesive disposed on the inner surface of the base means capable of securely attaching the support to the tissue; and an elastic substrate having an inner surface and an outer surface wherein the inner surface of the elastic substrate is fixedly attached to and covers at least a portion of the outer surface of the base means, and wherein the outer surface of the elastic substrate is not masked by any other substrate when in use. Preferably, the adhesive is hypoallergenic and the base means is porous. Further, the elastic substrate is preferably loop material with an acrylic or starch binder.

The advantages of the support device of the invention can also be enjoyed in applications in which greater support is needed, for example, for lifting and stabilizing larger anatomical parts, such as a breast, buttock or herniated area. Thus, the support device can further include one or more internalized bands disposed between the adhesive base plate and the elastic substrate. The elastic substrate may be a loop material having a fabric backing. A plurality of bands can extend along the length of the support device or transversely across the width. The bands can be constructed of plastic, polymer material, wire or thicker fabric material. The loop material can also be utilized to add further layers of fabric or support strips to vary the level of support rigidity of the device.

Thus, it is an object of the present invention to provide a universal anatomical support that can be used to support various tissues on the human body.

It is another object of the invention to provide a support having a medical grade adhesive which provides good adhesion to the skin and is hypoallergenic.

It is yet another object of the invention to provide a support having an adhesive which leaves no sticky residue on the user's skin.

It is still another object of the invention to provide a support which is water resistant and less likely to separate from the skin when the user perspires or showers, improving use for sleeping and vigorous athletic applications.

It is yet a further object of the invention to provide a support which conforms and stretches to the contours of the tissue being supported.

It is still a further object of the invention to provide a support having a medical grade adhesive tape that is porous and allows oxygen to reach the user's skin.

Yet another object of the invention is to provide a support which can be easily manufactured to have a wide range of elasticities to satisfy a variety of tissue support applications.

It is another object of the invention to provide a support device which can be sterilized for potential use in the operating room and other situations where a sterilized product is desired.

These and still other objects and advantages of the present invention will be apparent from the description below.

DETAILED DESCRIPTION OF THE INVENTION

As referred to herein, the inner surfaces of the various component parts of the preferred embodiments of the present invention are those surfaces oriented towards the object to which the support is adhered. Similarly, the outer surfaces of the various component parts of the preferred embodiments are those surfaces oriented away from such object.

Figure 1:
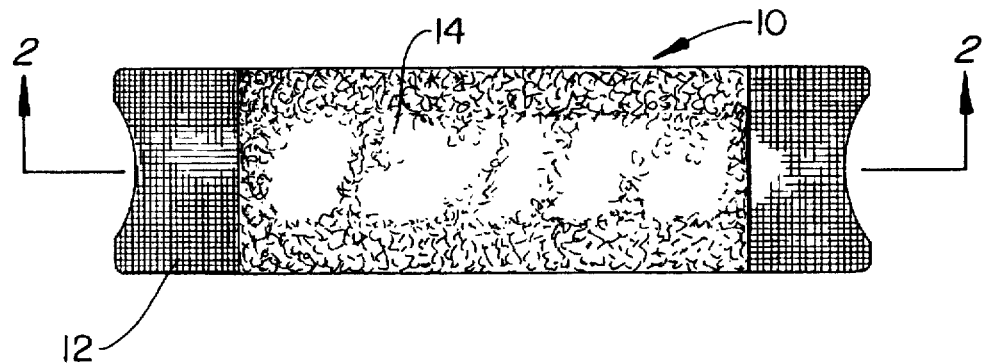
FIG. 1 is a top plan view of one version of the anatomical support of the present invention.
Figure 2:
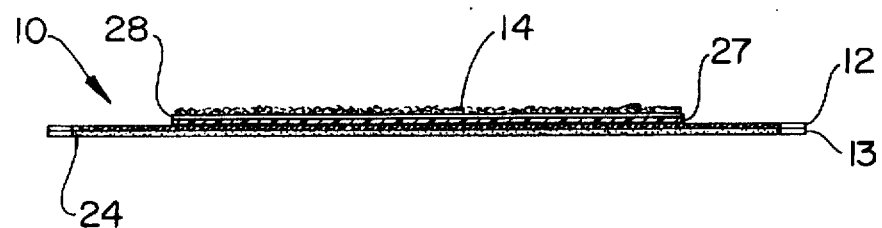
FIG. 2 is a cross-sectional view thereof, taken along line 2—2 of FIG. 1.
Figure 3:
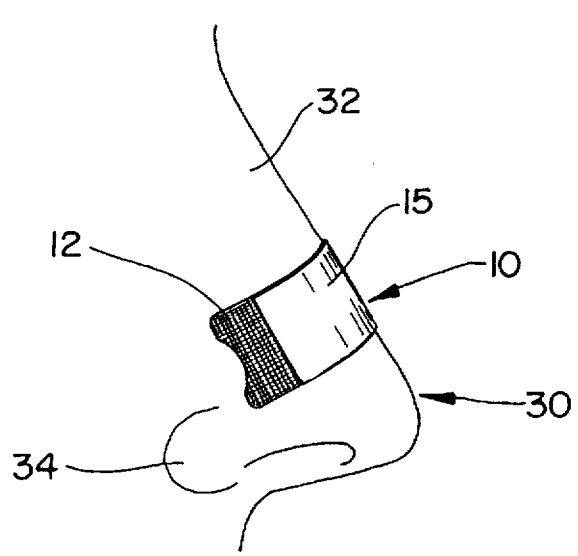
FIG. 3 is a side elevational view showing an example of one version of the present invention being used in a nasal application.
Figure 7:
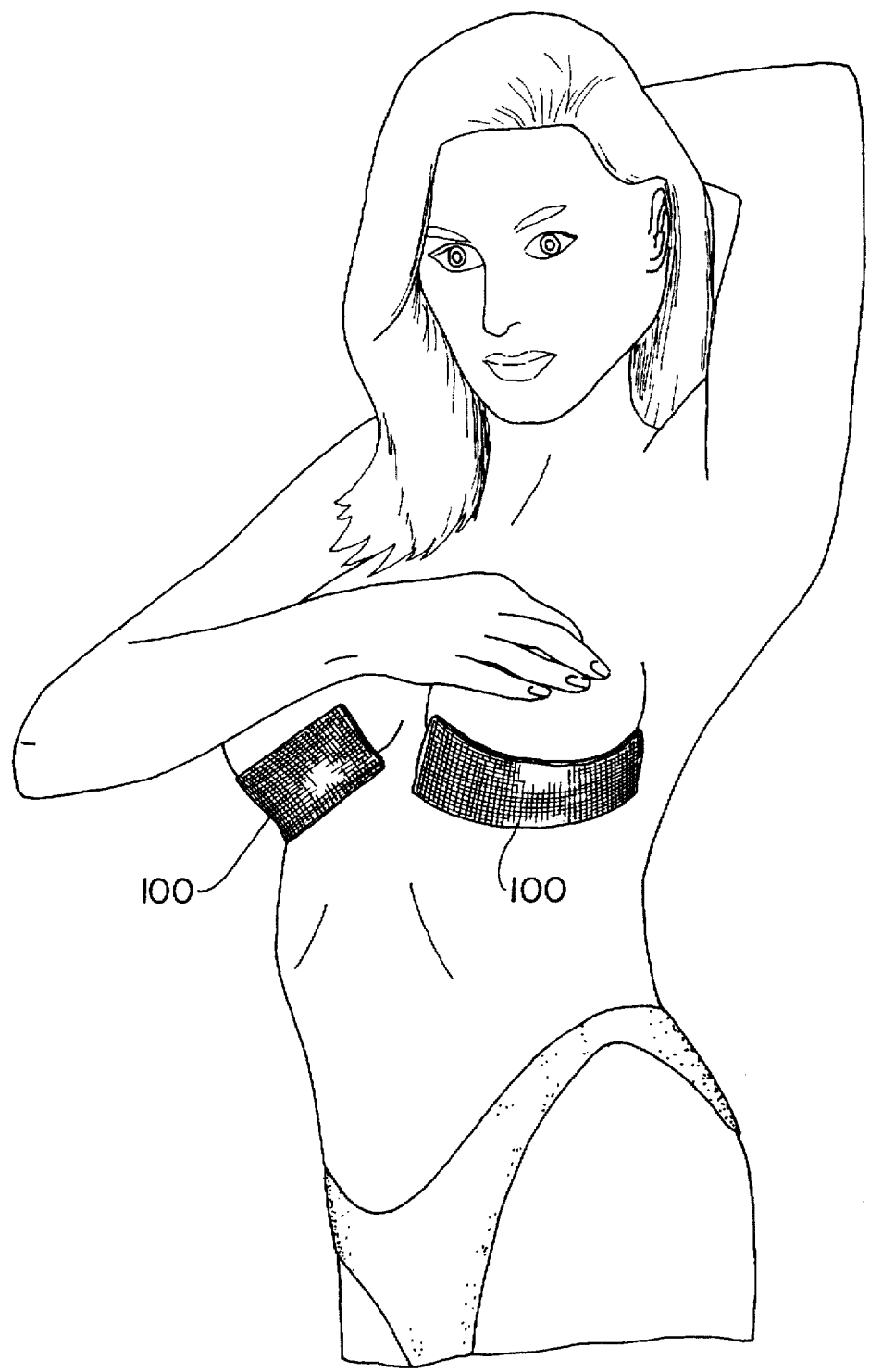
FIG. 7 illustrates an application of the invention for supporting breasts.

Referring now to FIGS. 1 and 2, there is shown an anatomical support, generally designated by reference numeral 10, according to a first preferred embodiment of the present invention. In the first preferred embodiment, support 10 can be particularly suitable for use as a support for nostril tissue as depicted in FIG. 3 or as a support for larger tissue, such as breasts as depicted in FIG. 7.

The base means for adhering the support 10 to the user's skin includes a base 12 that is preferably composed of medical grade tape such as 3M-1527L marketed by the 3M Company under the registered trademark TRANSPORE. Base 12 may also be other materials such as any medical grade, non-irritating, porous, adhesive material that will conform easily to anatomical body parts, including polyurethane bases.

Base 12 is coated on its inner surface 24 with a medical grade adhesive, preferably a hypoallergenic ethylene/vinyl acetate pressure sensitive adhesive. Preferably, the base 12 is perforated or porous such that oxygen is able to reach the user's skin. Preferably, the base also conforms and stretches to adapt to the contours of tissue anywhere on the human anatomy.

Referring to FIG. 2, an elastic substrate such as a loop pad 14 is fixedly attached to a loop fabric backing or a binder 28 which in turn includes transfer tape 27 for fixedly attaching the loop fabric to the outside surface of base 12. The transfer tape 27 can be, for example, a thin, high tack, double-coated pressure sensitive film tape, such as Adhesive Research AR Care 7737. A preferred loop material is available from the Velcro USA under the model Loop #3003. The loop material 14, its fabric backing 28, and transfer tape 27 cover at least a portion of the outer surface of base 12. Coverage of this outer surface by the loop material composite can be varied depending on the desired elasticity of the support 10. For example, providing greater coverage of base 12 by the loop material composite tends to give the support 10 greater elasticity.

The loop material 14 and its fabric backing 28 are designed to provide elasticity to the support 10. In other words, when the support 10 is deformed to adapt to the user's anatomical features, the loop material composite has a tendency to revert to its original shape and, thereby, exert an outward force from the user's skin. Thus, any elastic substrate might be advantageous for the present invention. Other examples of elastic substrates that might be acceptable substitutes for the loop material 14 and fabric backing 28 of the present invention include plastic strips, any fabric, plastic-coated or woven material that can stabilize, is malleable and can conform easily to anatomical body parts, is water-resistant and sterilizable. The alternative elastic substrates can have any combination of these features.

Also shown in FIG. 2 is liner 13 which is disposed on the inner portion of base 12 to protect the adhesive surface thereof. When the support is to be used and to be adhered to an anatomical feature of the user or elsewhere, liner 13 is removed and fresh adhesive on surface 24 of base 12 is exposed.

For application of the support for a larger anatomical structures, such as for larger breast support (see FIG. 7), the support 10 can be constructed with an acrylic or starch binder coat 28 applied directly to the loop material 14. This binder coat is preferably applied prior to the application of the pressure sensitive adhesive 27 to provide further body and strength to the support 10.

Turning now to FIG. 3, a method of using one version of the anatomical support of the present invention is shown. Here, the anatomical support 10 is shown placed on a user's nose 30. The anatomical support 10 covers and is substantially centered between the user's nose bridge 32 and the end of the nose. The ends of the anatomical support 10 can overlap the flare of the nostril 34. When the anatomical support 10 is adhered to the user's nose 30, the elastic substrate, such as a flexible non-woven adhesive cover 15 tends to lift and stabilize the nose tissue to thereby support the nose tissues, allowing expansion of nasal passages and improving air flow.

It should be understood, that when the anatomical support of the present invention is used on a nose, that it lifts the tissue to thereby open the nasal passages allowing for improved breathing. Improved breathing can be important during physical activity or for those situations where user's have problems breathing due to congestion. One benefit that might be obtained with improved breathing is a decrease in nighttime snoring.

Variations of the above-described version of the anatomical support of the present invention can be used to provide lift and support to the tissue of other anatomical features. For example, the anatomical support can be used to lift and/or support breast tissue, hernia tissue, skin collections, and weakened joints due to illness or injury. The device can further be used for joint support during sports, support tissue during surgery to enhance the sterile field, buttock support, facial tissue support and eyelid support for patients with muscular disorders.

Figure 4:
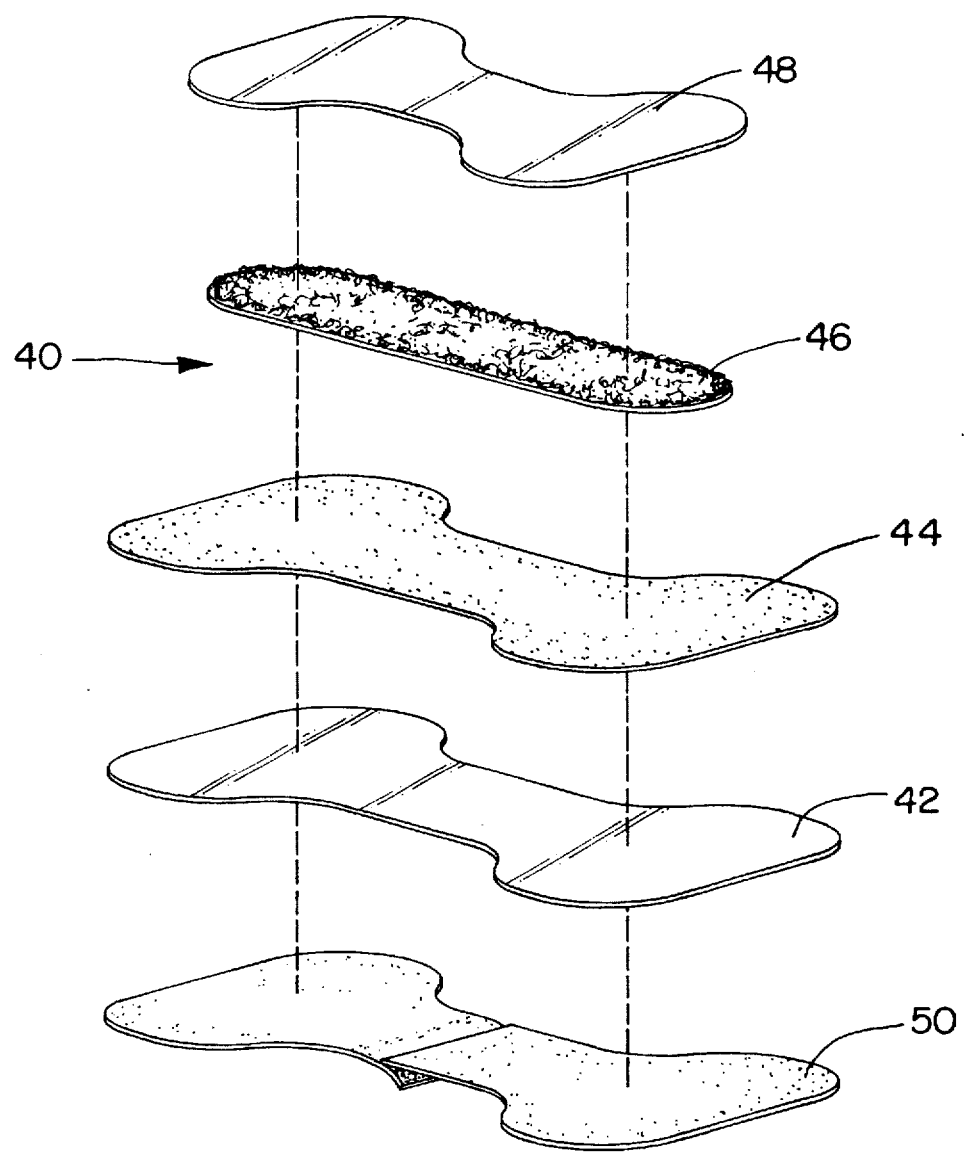
FIG. 4 is an exploded perspective view of still another embodiment of the invention utilizing molded hook material.

Referring to FIG. 4, an alternative support 40 for use in nasal applications can alternatively be constructed to provide a preferably porous, hypoallergenic tape base 42. An adhesive transfer tape 44 is preferably secured on its inner surface to the base 42. A molded hook material 46, with acrylic coat binder for support and resiliency, is preferably applied along the top of the adhesive tape 44 along the length of the tape 44 and base 42. The molded hook material 46 provides resiliency and is capable of conforming to a variety of nose geometries comfortably. The molded hook material 46 is preferably covered at least partially, by porous, non-woven material 48 having an adhesive backing. The base 42 can provide on its inner surface an adhesive that is protected prior to use by a removable liner 50.

Figure 5:
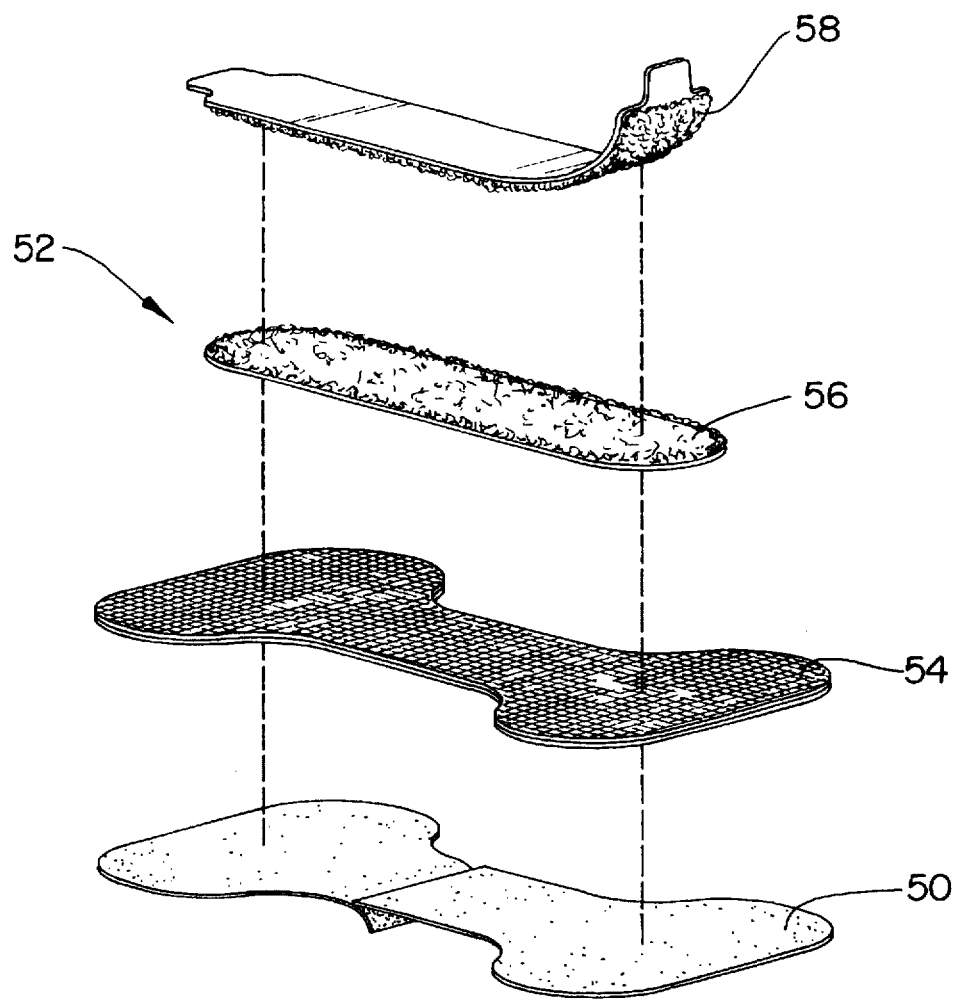
FIG. 5 is another exploded perspective view of an embodiment of the invention providing a variable tension strip.

Referring to FIG. 5, a further alternative support device 52 can be constructed to provide a hypoallergenic tape base 54 joined to a hook material member 56 by transfer tape and/or pressure sensitivity adhesive. The hook material member 56 is capable of interacting with a detachable loop material strip 58 providing mating loop material on its inner surface. The loop material strip 58 is preferably constructed with a stretchable elastic base that can be stretched prior to application to the hook material member 56, causing an inward pull on the support device 52 and an associated outward pull of the nasal passages when mounted to a nose, for example. The degree of tension achieved by the stretchable strip 58 can be adjusted to control the degree of nasal opening desired or required.

In the various embodiments, an elastic substrate is preferred because it provides a sufficiently rigid support to lift and stabilize certain tissue while avoiding the irritation associated with restricting rigid bands. This flexibility is advantageous in curved applications such as nasal tissue support, eyelid support and finger and joint support. In larger applications, where further rigid support is required, such as larger body parts as breasts and buttocks, it may be desirable to enjoy the benefits of the flexible loop material in combination with reinforcing bands or strips.

Figure 6:
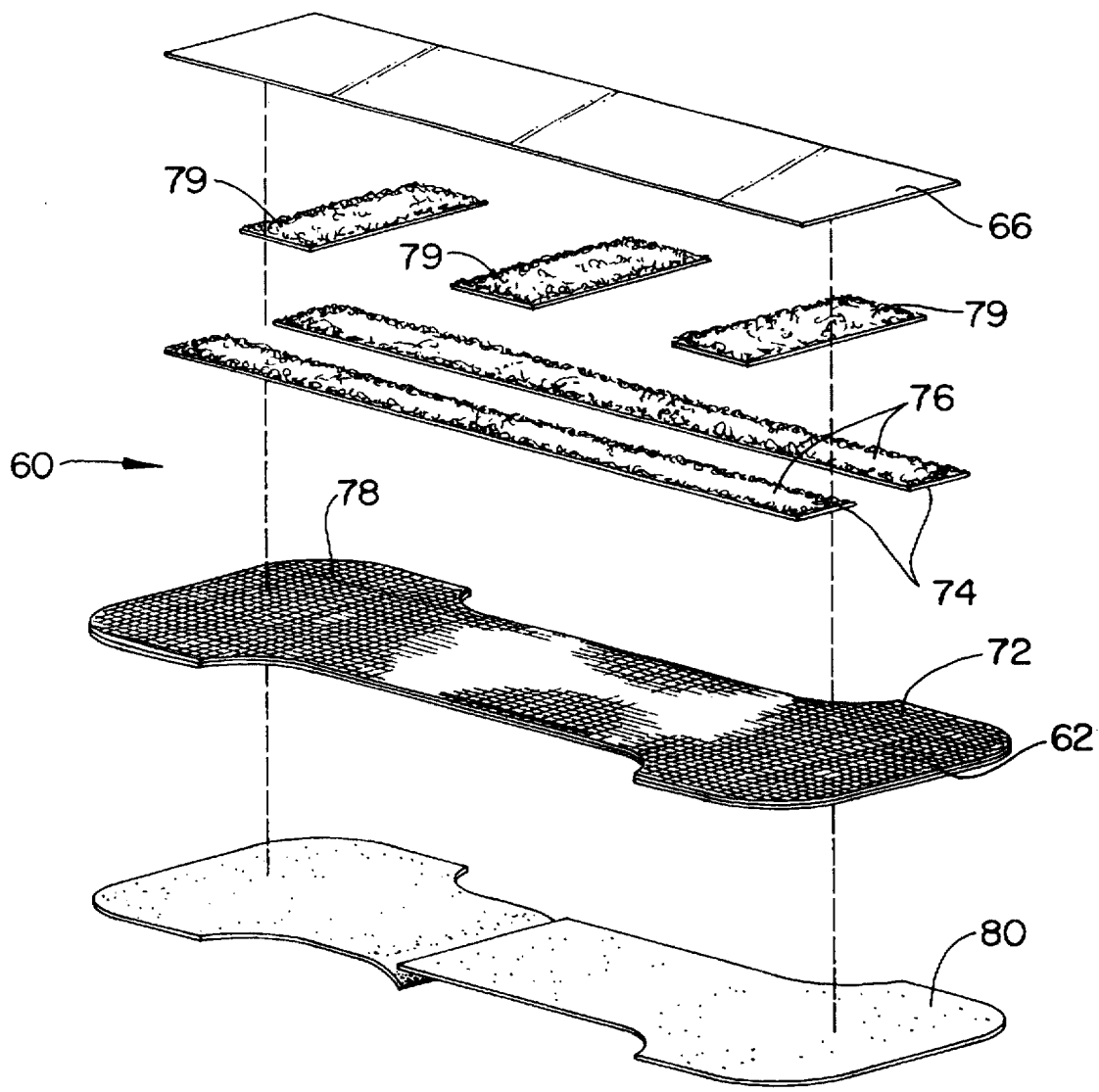
FIG. 6 is an exploded perspective view of an embodiment of the invention having detachable stiffening strips.

Referring to FIG. 6, an alternative embodiment in which an anatomical support 60 includes a base 62 coated on its inner surface with a medical-grade adhesive for connection to the user's skin. A cover 66 of a non-porous non-woven material can be secured to the outside surface 72 of the base 62 by transfer tape or pressure sensitive adhesive. Disposed between the cover 66 and the base 62 are one or more reinforcing strips 74 that can be constructed from a variety of materials including plastic, polymer materials, wire or thicker loop material.

The strips 74 are preferably secured to the cover 66 and base 72 by tape or pressure sensitive adhesive. Alternative arrangements are also contemplated, including providing a plurality of strips longitudinally or strips 79 transversely across the width of the support to provide different support configuration.

The adhesive surface of the base 62 can be covered by a release liner 80, which is preferably the Flex Mark 78 B Mando release liner manufactured by Flexcon Company. Other release liners for covering the adhesive until use can also be used.

Referring to FIG. 7, another preferred application of the support device is to provide underlying breast support, for use particularly in applications where a brassiere or other breast support is not practical or possible. The breast support 10 can be used, for example, in connection with backless evening gowns or swimwear. In a preferred water resistant construction, the breast support can be particularly advantageous for swimming activities. The breast support can be made in varying sizes to accommodate different breast sizes and the construction can be cut by scissors or the like to accommodate users preferences.

The various embodiments of the invention have been set forth above with a great degree of particularity. Additional alternatives may now be apparent to one having ordinary skill in the art on the basis of this teaching. It is intended that the invention not be limited to the specific embodiments set forth. Therefore, the scope of the claims is should not be determined by the specific examples of the preferred versions herein. Rather, the claims should be looked to in order to judge the full scope of the invention.

I claim:

1. A method of lifting or supporting tissue of an anatomical feature on a subject comprising:

placing a support on the tissue of the anatomical feature wherein the support comprises a base means for adhering the support to the tissue, the base means having an inner surface carrying an inwardly facing adhesive for fixedly attaching the support to the tissue and an outer surface having fixedly attached thereto, on at least a portion thereof, an elastic member including one of a hook and loop material on an outwardly facing mating surface adapted to removably attach to a mating material.

2. The method of claim 1, wherein the adhesive is hypoallergenic.

3. The method of claim 2, wherein the base means is porous.

4. The method of claim 1, wherein the anatomical feature is a nose.

5. The method of claim 4, wherein the support is adhered and substantially centered over the nose between the bridge and end of the nose.

6. The method of claim 5, wherein the elastic member includes a porous non-woven cover over the one of loop and hook material.

7. The method of claim 6, wherein said one of hook and loop material includes a binder of one of acrylic and starch.

8. The method of claim 1, further comprising a strip having a mating material of one of hook and loop material for detachably connecting to said one of hook and loop material of said elastic member, said mating material being mounted on a stretchable backing for applying variable degrees of tension of the support.

9. The method of claim 1, wherein the anatomical feature is a breast.

10. The method of claim 9, wherein the one of a loop and hook material has a fabric backing, said one of a loop and hook material being reinforced by a starch binder.

11. A support for lifting or supporting tissue of an anatomical feature on a subject comprising:

a base for adhering the support to the tissue, the base having an inner surface and an outer surface;

an adhesive disposed on the inner surface of the base capable of fixedly attaching the support to the tissue;

an elastic member having one of hook and loop material having a fabric backing, said elastic member having an inner surface and an outer surface wherein the inner surface of the elastic member is fixedly attached to and covers at least a portion of the outer surface of the base; and a removable strip having at least one of hook and loop material for detachably mating and connecting to said elastic member, said strip being mounted on a stretchable backing for applying variable degrees of tension to the base when connected to said elastic member.

12. The support of claim 11, wherein the adhesive is hypoallergenic.

13. The support of claim 11, wherein the base means is porous.

14. The support of claim 11, wherein the hook and loop material is reinforced by a coat of at least one of starch and acrylic.

15. The support of claim 14, wherein reinforcing bands are mounted longitudinally along the base.

16. The support of claim 14, wherein reinforcing bands are mounted transversely across the base.

* * * * *